US008569241B2

(12) United States Patent
Ohsawa et al.

(10) Patent No.: US 8,569,241 B2
(45) Date of Patent: Oct. 29, 2013

(54) COMPOSITION FOR IMPROVING BRAIN FUNCTION AND METHOD FOR IMPROVING BRAIN FUNCTION

(75) Inventors: Kazuhito Ohsawa, Sagamihara (JP); Naoto Uchida, Sagamihara (JP); Kohji Ohki, Sagamihara (JP); Hiroaki Goto, Sagamihara (JP)

(73) Assignee: Calpis Co., Ltd., Tokyo (JP)

( * ) Notice: Subject to any disclaimer, the term of this patent is extended or adjusted under 35 U.S.C. 154(b) by 0 days.

(21) Appl. No.: 13/532,394

(22) Filed: Jun. 25, 2012

(65) Prior Publication Data

US 2012/0277160 A1     Nov. 1, 2012

Related U.S. Application Data

(63) Continuation of application No. PCT/JP2010/065483, filed on Sep. 9, 2010.

(30) Foreign Application Priority Data

Dec. 28, 2009  (JP) ................................. 2009-297022
Jun. 29, 2010  (JP) ................................. 2010-147156

(51) Int. Cl.
*A01N 37/18*       (2006.01)
*A61K 38/00*       (2006.01)
*C07K 16/00*       (2006.01)

(52) U.S. Cl.
USPC ........ 514/17.7; 514/17.5; 514/17.6; 530/322; 530/300

(58) Field of Classification Search
None
See application file for complete search history.

(56) References Cited

U.S. PATENT DOCUMENTS

| 6,994,987 B1 | 2/2006 | Yamamoto et al. |
| 2006/0154871 A1 | 7/2006 | Georgiades |
| 2008/0107775 A1 | 5/2008 | Prakash et al. |
| 2011/0046015 A1 | 2/2011 | Honda et al. |
| 2011/0092431 A1 | 4/2011 | Ohsawa et al. |

FOREIGN PATENT DOCUMENTS

| EP | 2 123 666 A1 | 11/2009 |
| EP | 2 258 208 A1 | 12/2010 |
| JP | 3-31298 A | 2/1991 |
| JP | 6-41191 A | 2/1994 |
| JP | 2001-64197 A | 3/2001 |
| JP | 2001-136995 A | 5/2001 |
| JP | 2003-520771 A | 7/2003 |
| JP | 3898389 B2 | 3/2007 |
| JP | 2008-214242 A | 9/2008 |
| WO | WO 00/75173 A2 | 12/2000 |
| WO | WO 01-55199 A1 | 8/2001 |
| WO | WO 02/46211 A2 | 6/2002 |
| WO | WO 2008/057964 A2 | 5/2008 |
| WO | WO 2009/096490 A1 | 8/2009 |
| WO | WO 2009/130349 A1 | 10/2009 |
| WO | WO 2010/071132 A1 | 6/2010 |

OTHER PUBLICATIONS

Asano, et al., "Inhibition of Prolyl Endopeptidase by Synthetic Peptide Fragments of Human Beta-casein", Argic Biol Chem, 1991, vol. 55, No. 3, pp. 825-828.
Bartus, et al., "The Cholinergic Hypothesis of Geriatric Memory Dysfunction", Science, Jul. 1982, vol. 217, pp. 408-417.
Becker, et al., "dTyr-D-Phe3 (Pro-D-Phe-Pro-Gly) Interacts Specifically With Amygdaloid-Kindled Seizures and Is Capable of Preventing the Learning Deficit Occuring After Kindling", Peptides, 1992, vol. 13, pp. 73-76.
Form PCT/ISA/210 for PCT/JP2010/065483 dated Nov. 22, 2010.
Form PCT/ISA/237 for PCT/JP2010/065483 dated Nov. 22, 2010.
Nakamura, "Functions and Utilization of Lactic Acid Bacteria, Physiological Function of Calpis Sour Milk", Food processing and Ingredients, 1999, vol. 34, No. 2, pp. 12-14.
Office Action of JP 2011-119960 dated Jan. 19, 2012.
Office Action of JP 2011-520254 dated Jul. 21, 2011.
Ohsawa, et al., "*Lactobacillus helveticus* Hakkonyu No Kioku Shogai Yobo Oyobi Kiokuryoku Kojo Sayo", The Japanese Society of Nutrition and Food Science Taikai Koen Yoshishu, 2010, vol. 64, pp. 121.
Sakaguchi, et al., "Effects of Systemic Administration of B-casomorphin-5 on Learning and Memory in Mice", European Journal of Pharmacology, 2006, vol. 530, No. 1-2, pp. 81-87.
Takano, "Health Effects of Milk Fermented by *Lactobacillus helveticus*", Milk Science, 2005, vol. 54, No. 3, pp. 141-144.
Extended European Search Report issued in European Patent Application No. 10840806.3 on Jun. 3, 2013.
Jørgensen et al., "Colostrum and bioactive, colostral peptides differentially modulate the innate immune response of intestinal epithelial cells", Journal of Peptide Science, vol. 16 (2010) pp. 21-30.

*Primary Examiner* — Olga N Chernyshev
(74) *Attorney, Agent, or Firm* — Birch, Stewart, Kolasch & Birch, LLP

(57) ABSTRACT

Provided are a composition for improving the brain function, which can be orally taken at a low dose, and a method therefor. The composition for improving the brain function contains, as the active ingredient, X-Pro-Pro-Leu-Thr-Gln-Thr-Pro-Val-Val-Val-Pro-Pro-Phe-Leu-Gln-Pro-Glu-Y (wherein X is nil or represents Ile or Asn-Ile; and Y is nil or represents Val-Met), X-Val-Val-Val-Pro-Pro-Phe-Leu-Gln-Pro-Glu-Y (wherein X is absent or represents Thr-Gln-Thr-Pro, Pro-Leu-Thr-Gln-Thr-Pro, Leu-Thr-Gln-Thr-Pro or Pro; and Y is absent or represents Val-Met), or a salt of the same. The method for improving the brain function comprises administering said peptide or a salt of the same.

18 Claims, 6 Drawing Sheets

COMPOSITION FOR IMPROVING BRAIN FUNCTION AND METHOD FOR IMPROVING BRAIN FUNCTION

CROSS-REFERENCE TO RELATED APPLICATIONS

This application is a Continuation of PCT International Application No. PCT/JP2010/065483 filed on Sep. 9, 2010, which claims priority of Application No. 2009 297022 filed in Japan on Dec. 28, 2009 and Application No. 2010-147156 filed in Japan on Jun. 29, 2010, all which are hereby expressly incorporated by reference into the present application.

BACKGROUND OF THE INVENTION

The present invention relates to a composition for improving brain function and a method for improving brain function.

BACKGROUND ART

The symptoms and diseases caused by a deterioration of brain function include depression, schizophrenia, delirium, dementia (cerebrovascular dementia, Alzheimer's disease, and the like), and the like. With the aging of the population in modern society, especially the increase in the number of dementia patients is becoming a serious social issue. Dementia symptoms vary depending on patients, but symptoms commonly observed include dysmnesia, disorientation, decline in judgment and thinking ability, and the like. The forms of dementia having especially a large number of patients are cerebrovascular dementia and Alzheimer's disease. For example, in the cerebrovascular dementia, damage to the nerve cells in the cerebral cortex and hippocampus caused by obstruction of the brain blood flow gives a rise to cognitive impairment and dysmnesia. For this reason, in addition to treating pre-existing diseases such as high-blood pressure, diabetes, and hypercholesterolemia, which may trigger cerebrovascular disorders, drugs for improving brain blood flow and/or drugs for protecting brain nerve cells are administered. In the meantime, causes of Alzheimer's disease have not been clearly elucidated; however, since a decrease in the level of acetylcholine, which is a neurotransmitter in the brain, is observed in the patients with this disease, a hypofunction of cholinergic neurons is assumed to be one of the causes (for example, Science, 217, 408-414 (1982)). Therefore, a therapeutic strategy aiming at preventing the hypofunction of cholinergic neurons by increasing the concentration of acetylcholine has been the mainstream for the treatment of Alzheimer's disease.

Currently, as a therapeutic drug against Alzheimer's disease, acetylcholinesterase inhibitors, for example, such as donepezil hydrochloride, are commercially available. However, the acetylcholinesterase inhibitors, such as donepezil hydrochloride, have their drawbacks that they should not be administered for an extended period of time due to their hepatotoxicity and strong side-effects as well as that they are costly.

Meantime, as a report on peptides showing anti-amnesic effect, for example, it has been reported that XPLPR (X represents L, I, M, F, or W) (SEQ ID NO: 17) demonstrated curative effects on scopolamine-induced amnesia when administered intracerebroventricularly or orally at 300 mg/kg, and, a release of acetylcholine from the intracerebral C3a receptor has been suggested as one of the mechanisms involved in this effect (Japanese Patent No. 3898389). Scopolamine is believed to function as a muscarinic receptor antagonist that induces the hypofunction of cholinergic neurons. Working as an inducer of brain dysfunction, scopolamine is used in the production of model animals to be used in the development of therapeutic drugs against Alzheimer's disease. In regard to the prophylactic and/or curative actions against brain dysfunction by the action of scopolamine, their effects may be demonstrated in behavioral pharmacological tests, such as a Y-shaped maze test, an eight-arm maze test, a passive avoidance test. Further, the effects of improving and/or strengthening brain function may be demonstrated in the same behavioral pharmacological tests with use of normal animals. However, all these peptides need to be administered at a high dose orally, intraabdominally, intracerebroventricularly, or the like in order to demonstrate their actions; therefore, they are not considered to be orally ingestible substances capable of demonstrating a sufficient level of effects. In addition, there has been no report on evaluation of peptides of the present invention and their analogs; therefore, their actions for the improvement of brain function have been hitherto unknown.

Thus, with the progress of the aging of the society, there has been strongly increasing demands for development of pharmaceutical agents, which prevent the symptoms and diseases due to a deterioration of brain function and further demonstrate curative effects on the symptoms and diseases, and for further development of safer compounds excellent in food application.

SUMMARY OF INVENTION

The present invention provides a composition which is ingestible orally at a low dose for the purpose of improving brain function. Further, the present invention provides a method for improving brain function. Several aspects of the present invention are as follows.

(1) An aspect of the present invention is a composition for improving brain function, the composition comprising, as an active ingredient, X-Pro-Pro-Leu-Thr-Gln-Thr-Pro-Val-Val-Val-Pro-Pro-Phe-Leu-Gln-Pro-Glu-Y (SEQ ID NO:20) (wherein X is absent or represents either Ile or Asn-Ile, and Y is absent or represents Val-Met) (SEQ ID NO: 1 to 6) or a salt thereof.

(2) An aspect of the present invention is a composition for improving brain function, the composition comprising, as an active ingredient, Pro-Pro-Leu-Thr-Gln-Thr-Pro-Val-Val-Val-Pro-Pro-Phe-Leu-Gln-Pro-Glu (SEQ ID NO: 1) or a salt thereof.

(3) An aspect of the present invention is a composition for improving brain function, the composition comprising, as an active ingredient, Ile-Pro-Pro-Leu-Thr-Gln-Thr-Pro-Val-Val-Val-Pro-Pro-Phe-Leu-Gln-Pro-Glu (SEQ ID NO: 2) or a salt thereof.

(4) An aspect of the present invention is a composition for improving brain function, the composition comprising, as an active ingredient, Asn-Ile-Pro-Pro-Leu-Thr-Gln-Thr-Pro-Val-Val-Val-Pro-Pro-Phe-Leu-Gln-Pro-Glu (SEQ ID NO: 3) or a salt thereof.

(5) An aspect of the present invention is a composition for improving brain function, the composition comprising, as an active ingredient, Asn-Ile-Pro-Pro-Leu-Thr-Gln-Thr-Pro-Val-Val-Val-Pro-Pro-Phe-Leu-Gln-Pro-Glu-Val-Met (SEQ ID NO: 6) or a salt thereof.

(6) An aspect of the present invention is a composition for improving brain function, the composition comprising, as an active ingredient, X-Val-Val-Val-Pro-Pro-Phe-Leu-Gln-Pro-Glu-Y (SEQ ID NO:21) (wherein X is absent or represents any of Thr-Gln-Thr-Pro (SEQ ID NO:22), Pro-Leu-Thr-Gln- Thr-Pro (SEQ ID NO:23), Leu-Thr-Gln-Thr-Pro (SEQ ID NO:24), and Pro, and Y is absent or represents Val-Met) (SEQ ID NO: 7 to 16) or a salt thereof.

(7) An aspect of the present invention is a composition for improving brain function, the composition comprising, as an active ingredient, Thr-Gln-Thr-Pro-Val-Val-Val-Pro-Pro-Phe-Leu-Gln-Pro-Glu (SEQ ID NO: 7) or a salt thereof.

(8) An aspect of the present invention is a composition for improving brain function, the composition comprising, as an active ingredient, Pro-Leu-Thr-Gln-Thr-Pro-Val-Val-Val-Pro-Pro-Phe-Leu-Gln-Pro-Glu (SEQ ID NO: 8) or a salt thereof.

(9) An aspect of the present invention is a composition for improving brain function, the composition comprising, as an active ingredient, Leu-Thr-Gln-Thr-Pro-Val-Val-Val-Pro-Pro-Phe-Leu-Gln-Pro-Glu (SEQ ID NO: 9) or a salt thereof.

(10) An aspect of the present invention is a composition for improving brain function, the composition comprising, as an active ingredient, Pro-Val-Val-Val-Pro-Pro-Phe-Leu-Gln-Pro-Glu (SEQ ID NO: 10) or a salt thereof.

(11) An aspect of the present invention is a composition for improving brain function, the composition comprising, as an active ingredient, Val-Val-Val-Pro-Pro-Phe-Leu-Gln-Pro-Glu (SEQ ID NO: 11) or a salt thereof.

(12) An aspect of the present invention is also the composition described in any one of (1) to (11), in which the composition is for oral ingestion.

(13) Especially, an aspect of the present invention is the composition described in any one of (1) to (12), in which the improving brain function is preventing amnesia or strengthening memory.

(14) An aspect of the present invention is also a method for improving brain function, the method comprising administering to a non-human animal X-Pro-Pro-Leu-Thr-Gln-Thr-Pro-Val-Val-Val-Pro-Pro-Phe-Leu-Gln-Pro-Glu-Y (wherein X is absent or represents either Ile or Asn-Ile, and Y is absent or represents Val-Met) or a salt thereof.

(15) An aspect of the present invention is also a method for improving brain function, the method comprising administering to a non-human animal Pro-Pro-Leu-Thr-Gln-Thr-Pro-Val-Val-Val-Pro-Pro-Phe-Leu-Gln-Pro-Glu or a salt thereof.

(16) An aspect of the present invention is especially also a method for improving brain function, the method comprising administering to a non-human animal Ile-Pro-Pro-Leu-Thr-Gln-Thr-Pro-Val-Val-Val-Pro-Pro-Phe-Leu-Gln-Pro-Glu or a salt thereof.

(17) An aspect of the present invention is also a method for improving brain function, the method comprising administering to a non-human animal Asn-Ile-Pro-Pro-Leu-Thr-Gln-Thr-Pro-Val-Val-Val-Pro-Pro-Phe-Leu-Gln-Pro-Glu or a salt thereof.

(18) An aspect of the present invention is also a method for improving brain function, the method comprising administering to a non-human animal Asn-Ile-Pro-Pro-Leu-Thr-Gln-Thr-Pro-Val-Val-Val-Pro-Pro-Phe-Leu-Gln-Pro-Glu-Val-Met or a salt thereof.

(19) An aspect of the present invention is also a method for improving brain function, the method comprising administering X-Val-Val-Val-Pro-Pro-Phe-Leu-Gln-Pro-Glu-Y (wherein X is absent or represents any of Thr-Gln-Thr-Pro, Pro-Leu-Thr-Gln-Thr-Pro, Leu-Thr-Gln-Thr-Pro, and Pro, and Y is absent or represents Val-Met) or a salt thereof.

(20) An aspect of the present invention is also a method for improving brain function, the method comprising administering to a non-human animal Thr-Gln-Thr-Pro-Val-Val-Val-Pro-Pro-Phe-Leu-Gln-Pro-Glu or a salt thereof.

(21) An aspect of the present invention is also a method for improving brain function, the method comprising administering to a non-human animal Pro-Leu-Thr-Gln-Thr-Pro-Val-Val-Val-Pro-Pro-Phe-Leu-Gln-Pro-Glu or a salt thereof.

(22) An aspect of the present invention is also a method for improving brain function, the method comprising administering to a non-human animal Leu-Thr-Gln-Thr-Pro-Val-Val-Val-Pro-Pro-Phe-Leu-Gln-Pro-Glu or a salt thereof.

(23) An aspect of the present invention is also a method for improving brain function, the method comprising administering to a non-human animal Pro-Val-Val-Val-Pro-Pro-Phe-Leu-Gln-Pro-Glu or a salt thereof.

(24) An aspect of the present invention is also a method for improving brain function, the method comprising administering to a non-human animal Val-Val-Val-Pro-Pro-Phe-Leu-Gln-Pro-Glu or a salt thereof.

(25) An aspect of the present invention is also the method described in any one of (14) to (24), in which the administering is oral administration.

(26) Especially, an aspect of the present invention is also the method described in any one of (14) to (25), in which the improving brain function is preventing amnesia or strengthening memory.

DESCRIPTION OF EMBODIMENTS

Figure 1:
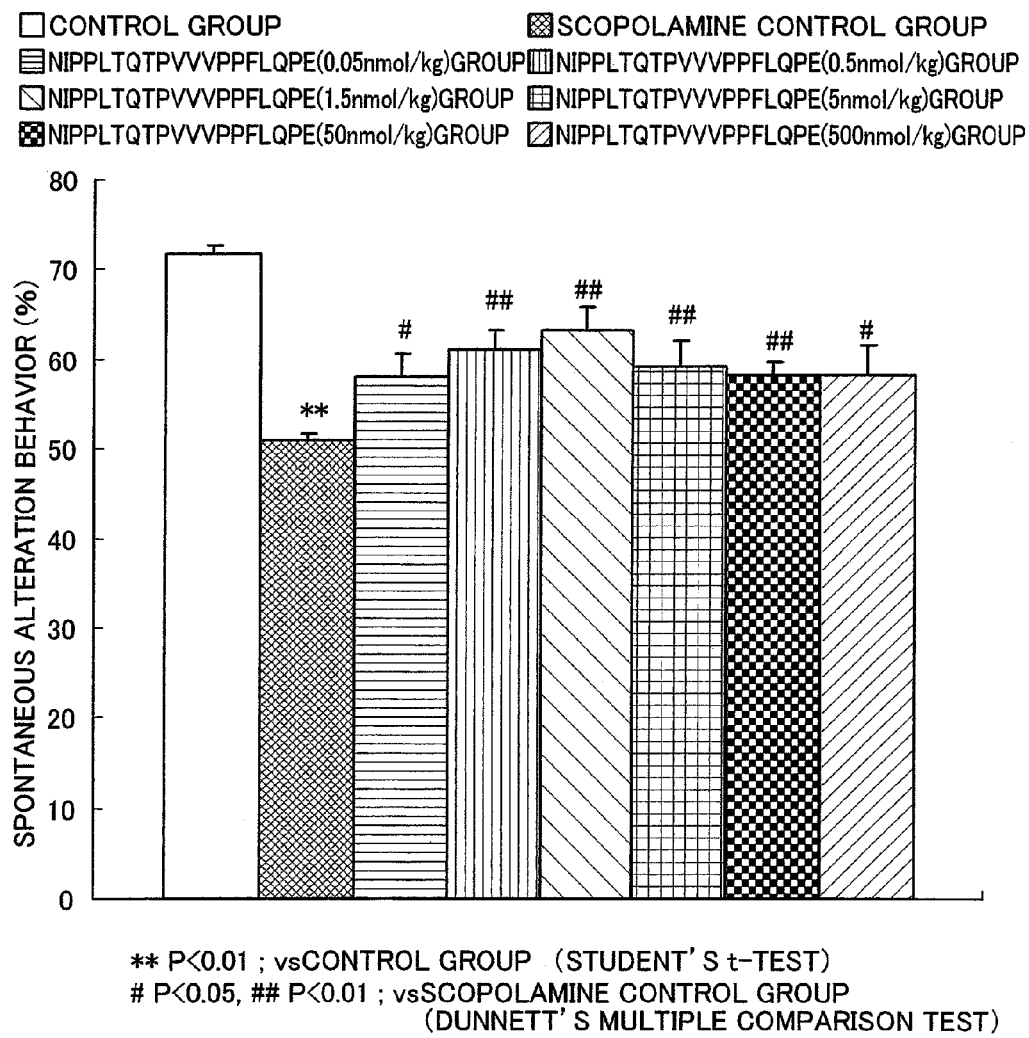
FIG. 1 shows a prophylactic effect of a peptide Asn-Ile-Pro-Pro-Leu-Thr-Gln-Thr-Pro- Val-Val-Val-Pro-Pro-Phe-Leu-Gln-Pro-Glu (NIPPLTQPVVVPPFLQPE) (SEQ ID NO: 3) against scopolamine-induced amnesia. Water (control), scopolamine alone, or 0.05 nmol/kg weight, 0.5 nmol/kg weight, 1.5 nmol/kg weight, 5 nmol/kg weight, 50 nmol/kg weight, or 500 nmol/kg weight of NIPPLTQTPVVVPPFLQPE (SEQ ID NO: 3) together with scopolamine was administered to mice, and their respective prophylactic effects against amnesia were evaluated in accordance with a method described in Example 1. The vertical axis in FIG. 1 shows the percentage of spontaneous alternation behavior. The percentage of spontaneous alternation behavior shown in the graph is of the control group, the scopolamine control group, and the NIPPLTQTPVVVPP-FLQPE-administered groups at 0.05 nmol/kg weight, 0.5 nmol/kg weight, 1.5 nmol/kg weight, 5 nmol/kg weight, 50 nmol/kg weight, and 500 nmol/kg weight in this order from the left. In order to confirm whether amnesia was induced, a significant difference between the scopolamine control group in which scopolamine was administered alone and the water-administered control group was calculated using Student's t-test. ** indicates P<0.01 with respect to the water-administered control group. A significant difference between the NIPPLTQTPVVVPPFLQPE-administered groups and the scopolamine control group was calculated using Dunnett's multiple comparison test. ## indicates P<0.01 with respect to the scopolamine control group.

A composition of the present invention includes, as an active ingredient, a peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or a peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly a peptide Asn-Ile-Pro-Pro-Leu-Thr-Gln-Thr-Pro-Val-Val-Val-Pro-Pro-Phe-Leu-Gln-Pro-Glu, a peptide Asn-Ile-Pro-Pro-Leu-Thr-Gln-Thr-Pro-Val-Val-Val-Pro-Pro-Phe-Leu-Gln-Pro-Glu-Val-Met, a peptide Ile-Pro-Pro-Leu-Thr-Gln-Thr-Pro-Val-Val-Val-Pro-Pro-Phe-Leu-Gln-Pro-Glu, a peptide Pro-Pro-Leu-Thr-Gln-Thr-Pro-Val-Val-Val-Pro-Pro-Phe-Leu-Gln-Pro-Glu, a peptide Thr-Gln-Thr-Pro-Val-Val-Val-Pro-Pro-Phe-Leu-Gln-Pro-Glu, a peptide Pro-Leu-Thr-Gln-Thr-Pro-Val-Val-Val-Pro-Pro-Phe-Leu-Gln-Pro-Glu, a peptide Leu-Thr-Gln-Thr-Pro-Val-Val-Val-Pro-Pro-Phe-Leu-Gln-Pro-Glu, a peptide Pro-Val-Val-Val-Pro-Pro-Phe-Leu-Gln-Pro-Glu, or a peptide Val-Val-Val-Pro-Pro-Phe-Leu-Gln-Pro-Glu. The peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) and the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe- Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, and the peptide Val-Val-Val-Pro-Pro-Phe-Leu-Gln-Pro-Glu, which are active ingredients, may be a chemically-synthesized peptide or a peptide derived from a natural product. For the chemical synthesis of these peptides, a commonly-used method, such as a solid phase synthesis (t-Boc-chemistry or Fmoc-chemistry) and a liquid phase synthesis, may be employed. For example, these peptides may be synthesized using an automated peptide synthesizer, such as the peptide synthesizer (PSSM-8) available from Shimadzu. A method for the peptide synthesis, appropriate reaction conditions, and the like may be selected based on the common general technical knowledge of a person skilled in the art at the discretion of the person. A method for purifying a chemically-synthesized peptide is also well known to those in the art.

As used in the specification, when referring to the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu, "X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly Asn-Ile-Pro-Pro-Leu-Thr-Gln-Thr-Pro-Val-Val-Val-Pro-Pro-Phe-Leu-Gln-Pro-Glu, Asn-Ile-Pro-Pro-Leu-Thr-Gln-Thr-Pro-Val-Val-Val-Pro-Pro-Phe-Leu-Gln-Pro-Glu-Val-Met, Ile-Pro-Pro-Leu-Thr-Gln-Thr-Pro-Val-Val-Val-Pro-Pro-Phe-Leu-Gln-Pro-Glu, Pro-Pro-Leu-Thr-Gln-Thr-Pro-Val-Val-Val-Pro-Pro-Phe-Leu-Gln-Pro-Glu, Thr-Gln-Thr-Pro-Val-Val-Val-Pro-Pro-Phe-Leu-Gln-Pro-Glu, Pro-Leu-Thr-Gln-Thr-Pro-Val-Val-Val-Pro-Pro-Phe-Leu-Gln-Pro-Glu, Leu-Thr-Gln-Thr-Pro-Val-Val-Val-Pro-Pro-Phe-Leu-Gln-Pro-Glu, or Pro-Val-Val-Val-Pro-Pro-Phe-Leu-Gln-Pro-Glu, or Val-Val-Val-Pro-Pro-Phe-Leu-Gln-Pro-Glu" and "the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu" include salts thereof unless otherwise clearly indicated or otherwise obvious within the context that they should be excluded. Examples of such salts include salts, such as sodium salts, potassium salts, and hydrochloride salts, which may exist under physiological conditions. Meanwhile, the composition of the present invention may include other peptide and a free amino acid or a salt thereof, in addition to the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-G ln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu, which is the active ingredient of the composition of the present invention. In relation to the present invention, three-letter codes, single-letter codes, and peptide notation follow the general rules well known to those in the art.

The effect in improving brain function of the composition of the present invention, or the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu may be confirmed using a system based on an evaluation system for therapeutic drugs against Alzheimer's disease, the system using a Y-shaped maze test, for example. Specifically, a muscarinic receptor antagonist, such as scopolamine, may be used on a rat or a mouse so as to cause a hypofunction of the cholinergic neurons. Then, either the rat or the mouse may be given a drug, which induces amnesia by causing brain dysfunction, by itself, or the composition of the present invention, or X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly Asn-Ile-Pro-Pro-Leu-Thr-Gln-Thr-Pro-Val-Val-Val-Pro-Pro-Phe-Leu-Gln-Pro-Glu, Asn-Ile-Pro-Pro-Leu-Thr-Gln-Thr-Pro-Val-Val-Val-Pro-Pro-Phe-Leu-Gln-Pro-Glu-Val-Met, Ile-Pro-Pro-Leu-Thr-Gln-Thr-Pro-Val-Val-Val-Pro-Pro-Phe-Leu-Gln-Pro-Glu, Pro-Pro-Leu-Thr-Gln-Thr-Pro-Val-Val-Val-Pro-Pro-Phe-Leu-Gln-Pro-Glu, Thr-Gln-Thr-Pro-Val-Val-Val-Pro-Pro-Phe-Leu-Gln-Pro-Glu, Pro-Leu-Thr-Gln-Thr-Pro-Val-Val-Val-Pro-Pro-Phe-Leu-Gln-Pro-Glu, Leu-Thr-Gln-Thr-Pro-Val-Val-Val-Pro-Pro-Phe-Leu-Gln-Pro-Glu, Pro-Val-Val-Val-Pro-Pro-Phe-Leu-Gln-Pro-Glu, or Val-Val-Val-Pro-Pro-Phe-Leu-Gln-Pro-Glu together with such a drug; or, the rat or the mouse may be given, prior to the administration of such a drug, the composition of the present invention, or X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly Asn-Ile-Pro-Pro-Leu-Thr-Gln-Thr-Pro-Val-Val-Val-Pro-Pro-Phe-Leu-Gln-Pro-Glu, Asn-Ile-Pro-Pro-Leu-Thr-Gln-Thr-Pro-Val-Val-Val-Pro-Pro-Phe-Leu-Gln-Pro-Glu-Val-Met, Ile-Pro-Pro-Leu-Thr-Gln-Thr-Pro-Val-Val-Val-Pro-Pro-Phe-Leu-Gln-Pro-Glu, Pro-Pro-Leu-Thr-Gln-Thr-Pro-Val-Val-Val-Pro-Pro-Phe-Leu-Gln-Pro-Glu, Thr-Gln-Thr-Pro-Val-Val-Val-Pro-Pro-Phe-Leu-Gln-Pro-Glu, Pro-Leu-Thr-Gln-Thr-Pro-Val-Val-Val-Pro-Pro-Phe-Leu-Gln-Pro-Glu, Leu-Thr-Gln-Thr-Pro-Val-Val-Val-Pro-Pro-Phe-Leu-Gln-Pro-Glu, Pro-Val-Val-Val-Pro-Pro-Phe-Leu-Gln-Pro-Glu, or Val-Val-Val-Pro-Pro-Phe-Leu-Gln-Pro-Glu. Then, the rat or the mouse may be subjected to a test using a Y-shaped maze so that the prophylactic actions against amnesia of the composition of the present invention may be confirmed by using the percentage of spontaneous alternation behavior to different arms and the total number of entries into the maze as indicators.

In the tests, the negative control may be, for example, an animal receiving only water. In an experiment to confirm the prophylactic action against drug-induced amnesia of X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly Asn-Ile-Pro-Pro-Leu-Thr-Gln-Thr-Pro-Val-Val-Val-Pro-Pro-Phe-Leu-Gln-Pro-Glu, Asn-Ile-Pro-Pro-Leu-Thr-Gln-Thr-Pro-Val-Val-Val-Pro-Pro-Phe-Leu-Gln-Pro-Glu-Val-Met, Ile-Pro-Pro-Leu-Thr-Gln-Thr-Pro-Val-Val-Val-Pro-Pro-Phe-Leu-Gln-Pro-Glu, Pro-Pro-Leu-Thr-Gln-Thr-Pro-Val-Val-Val-Pro-Pro-Phe-Leu-Gln-Pro-Glu, Thr-Gln-Thr-Pro-Val-Val-Val-Pro-Pro-Phe-Leu-Gln-Pro-Glu, Pro-Leu-Thr-Gln-Thr-Pro-Val-Val-Val-Pro-Pro-Phe-Leu-Gln-Pro-Glu, Pro-Pro-Phe-Leu-Gln-Pro-Glu, or Val-Val-Val-Pro-Pro-Phe-Leu-Gln-Pro-Glu, an animal receiving only a drug, which induces amnesia by causing brain dysfunction, such as scopolamine, may be included to be used as a control.

The effect in improving brain function of the composition of the present invention, or the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu may be confirmed by a novel object recognition test using a rat or a mouse, for example. Specifically, either the rat or the mouse may be given the composition of the present invention, or the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu. Then, the rat or the mouse is subjected to a test using an experimental box. In the test, a training trial is performed in which the rat or the mouse is allowed to recognize two objects. Then, after a lapse of time to clear the memory, one object of the two objects is replaced with a novel one. In this situation, if the rat or the mouse remembers the object that has been replaced, the memory strengthening action of the composition of the present invention may be confirmed by using an increase in exploration time spent on the novel object as an indicator. In the tests, for example, an animal receiving only water may be included to be used as the negative control.

The composition of the present invention includes, as an active ingredient, the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu. Oral administration or oral ingestion thereof allows achievement of the desired effects described above. The period of administration or ingestion of the composition of the present invention may be variously adjusted upon consideration of the age of a target of the administration or ingestion, such as a human or non-human animal, and the health conditions and the like of the target. Examples of the non-human animal include non-human higher vertebrate animals, particularly non-human mammals, including pet animals, such as dogs and cats, and domestic animals, such as cattle, horses, pigs, and sheep; however, the non-human animal is not limited thereto. A single administration of the composition of the present invention is enough to demonstrate its effects; however, a continuous effect may be expected by continuous ingestion, which is once or more a day. The composition of the present invention when used as medicine may be in the form of drugs for oral administration. For example, the form may be a tablet, a pill, a hard capsule, a soft capsule, a microcapsule, a powder, a granule, a liquid, or the like. When produced as medicine, the composition of the present invention may be produced in a unit dose required for commonly-approved drug administration by, for example, including a pharmaceutically approved material, such as a carrier, an excipient, a filler, an antiseptic, a stabilizer, a binder, a pH modifier, a buffer, a thickener, a gellant, a preservative, and an antioxidant, accordingly as needed.

The composition of the present invention may also be used as a material for material for food and beverage or a material for animal feed. For example, the composition of the present invention, or the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu, which is the active ingredient of the composition of the present invention, may be considered a functional food, such as a food for specified health use, which is effective in improving brain function.

The dose of administration or ingestion of the present composition, or the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu in order to obtain desired effects is preferably 0.1 µg/kg weight to 1 mg/kg weight per administration or ingestion in general, in terms of the amount of the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu, which is the active ingredient. The dose per ingestion in a food, which is, for example, a functional food, may also be lowered further than the above-described level, depending on the number of ingestions per day. An appropriate dose of ingestion may be further adjusted upon consideration of various factors as described above.

The nutritional balance, flavors, and the like of a food, such as a functional food, including the composition of the present invention, or the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro- Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu, which is the active ingredient of the composition, may be improved, as needed, by addition of an additive either: made of other ingredient used in food, such as a saccharide, a protein, a lipid, a vitamin, a mineral, and a flavor, which include various carbohydrates, lipids, vitamins, minerals, sweeteners, flavoring agents, coloring agents, texture enhancers, and the like, for example; or made of a mixture thereof. Animal feed containing the composition of the present invention, or the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu, which is the active ingredient of the composition, may be prepared similarly to food for human consumption.

For example, the above-described functional food may have the form of a solid, a gel, or a liquid, may be in the form of, for example, any one of various processed foods and beverages, dry powder, a tablet, a capsule, a granule, and the like, and, further, may be any of various beverages, yogurt, a liquid food, jelly, a candy, a retort pouch food, a tablet confectionary, a cookie, a sponge cake, bread, a biscuit, a chocolate, and the like.

When a functional food, such as a food for specified health use, containing the composition of the present invention is manufactured, although depending on how the composition has been added and how the food containing the composition is served as a product, the functional food is prepared so that the amount of the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu, which is the active ingredient of the composition, to be contained in 100 g of the final product may be 1 µg to 10 g, preferably 10 µg to 1 g, more preferably 100 µg to 100 mg.

The composition of the present invention, or the peptide X-Pro-Pro-Leu-Thr-Gln-Thr-Pro-Val-Val-Val-Pro-Pro-Phe-Leu-Gln-Pro-Glu-Y (where X is absent or represents either Ile or Asn-Ile, and Y is absent or represents Val-Met) or the peptide X-Val-Val-Val-Pro-Pro-Phe-Leu-Gln-Pro-Glu-Y (where X is absent or represents any of Thr-Gln-Thr-Pro, Pro-Leu-Thr-Gln-Thr-Pro, Leu-Thr-Gln-Thr-Pro, and Pro, and Y is absent or represents Val-Met), particularly the peptide Asn-Ile-Pro-Pro-Leu-Thr-Gln-Thr-Pro-Val-Val-Val-Pro-Pro-Phe-Leu-Gln-Pro-Glu, the peptide Asn-Ile-Pro-Pro-Leu-Thr-Gln-Thr-Pro-Val-Val-Val-Pro-Pro-Phe-Leu-Gln-Pro-Glu-Val-Met, the peptide Ile-Pro-Pro-Leu-Thr-Gln-Thr-Pro-Val-Val-Val-Pro-Pro-Phe-Leu-Gln-Pro-Glu, the peptide Pro-Pro-Leu-Thr-Gln-Thr-Pro-Val-Val-Val-Pro-Pro-Phe-Leu-Gln-Pro-Glu, the peptide Thr-Gln-Thr-Pro-Val-Val-Val-Pro-Pro-Phe-Leu-Gln-Pro-Glu, the peptide Pro-Leu-Thr-Gln-Thr-Pro-Val-Val-Val-Pro-Pro-Phe-Leu-Gln-Pro-Glu, the peptide Leu-Thr-Gln-Thr-Pro-Val-Val-Val-Pro-Pro-Phe-Leu-Gln-Pro-Glu, the peptide Pro-Val-Val-Val-Pro-Pro-Phe-Leu-Gln-Pro-Glu, or the peptide Val-Val-Val-Pro-Pro-Phe-Leu-Gln-Pro-Glu, which is the active ingredient of the composition, may improve brain function, thereby being capable of preventing amnesia and strengthen memory. Further, the composition of the present invention or any one of the above-described peptides, which is the active ingredient of the composition, may also be used for treatment or prevention of the symptoms and diseases caused by a deterioration of brain function, the symptoms and diseases including depression, schizophrenia, delirium, dementia (cerebrovascular dementia, Alzheimer's disease, and the like), and the like.

Hereinafter, the present invention will be specifically described by ways of Examples; however, the scope of the invention is not limited to Examples.

EXAMPLE 1

Prophylactic Activity of Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE) Against Amnesia Male mice (n=15 to 75) of the ddY strain (approximately 7-week old) were used, and they received food and water ad lib. Test substances used were 0.05 nmol/kg weight (0.1 µg/kg weight), 0.5 nmol/kg weight (1 µg/kg weight), 1.5 nmol/kg weight (3 µg/kg weight), 5 nmol/kg weight (10 µg/kg weight), 50 nmol/kg weight (100 µg/kg weight), and 500 nmol/kg weight (1000 µg/kg weight) of Asn-Ile-Pro-Pro-Leu-Thr-Gln-Thr-Pro-Val-Val-Val-Pro-Pro-Phe-Leu-Gln-Pro-Glu. The test substances were administered to the mice once orally 60 minutes before the execution of a Y-shaped maze test for evaluation of spontaneous alternation behavior. Further, 30 minutes before the execution of the Y-shaped maze test, 1 mg/kg weight of scopolamine was subcutaneously administered on the backs of the mice in order to induce brain dysfunction (dysmnesia and/or cognitive impairment) in the mice. In the Y-shaped maze test, a Y-shaped maze was used as an experimental device, in which the length of each arm was 40 cm, the height of the wall was 12 cm, the width of the floor was 3 cm, and the width of the upper part was 10 cm, and three arms were connected to each other at an angle of 120 degrees. Each of the mice was placed at the tip of any one of the arms of the Y-shaped maze, and then let go to freely explore in the maze for 8 minutes. The sequence of the arms each of the mice entered was recorded. The number of entries by each of the mice for each of the arms during the measurement time was counted to be the total number of entries. In the sequence, the combination in which three different arms were selected in succession (for example, with the three arms respectively called A, B, and C, if the sequence of the arms entered is ABCBACACB, the count is 4 inclusive of overlapping) was investigated, and the number of the count was used as the number of spontaneous alternation behavior. The percentage of spontaneous alternation behavior was calculated by dividing the number of spontaneous alternation behavior by a number obtained by subtracting 2 from the total number of entries, and multiplying a resultant number by 100. The percentage of spontaneous alternation behavior was used as an indicator. A higher value of the indicator suggested better maintenance of short-term memory. The measured values were expressed in the form of mean±standard error for each group. A significant difference between the control group and the scopolamine control group was calculated using Student's t-test. Further, a significant difference between the scopolamine control group and the NIPPLTQTPVVVPPFLQPE-administered groups was calculated using Dunnett's multiple comparison test after one-way analysis of variance. Results are shown in FIG. 1. It was suggested that NIPPLTQTPVVVPPFLQPE had a prophylactic activity against amnesia when administered at a dose ranging from 0.05 nmol/kg weight to 500 nmol/kg weight (0.1 µg/kg weight to 1000 µg/kg weight).

EXAMPLE 2

Figure 2:
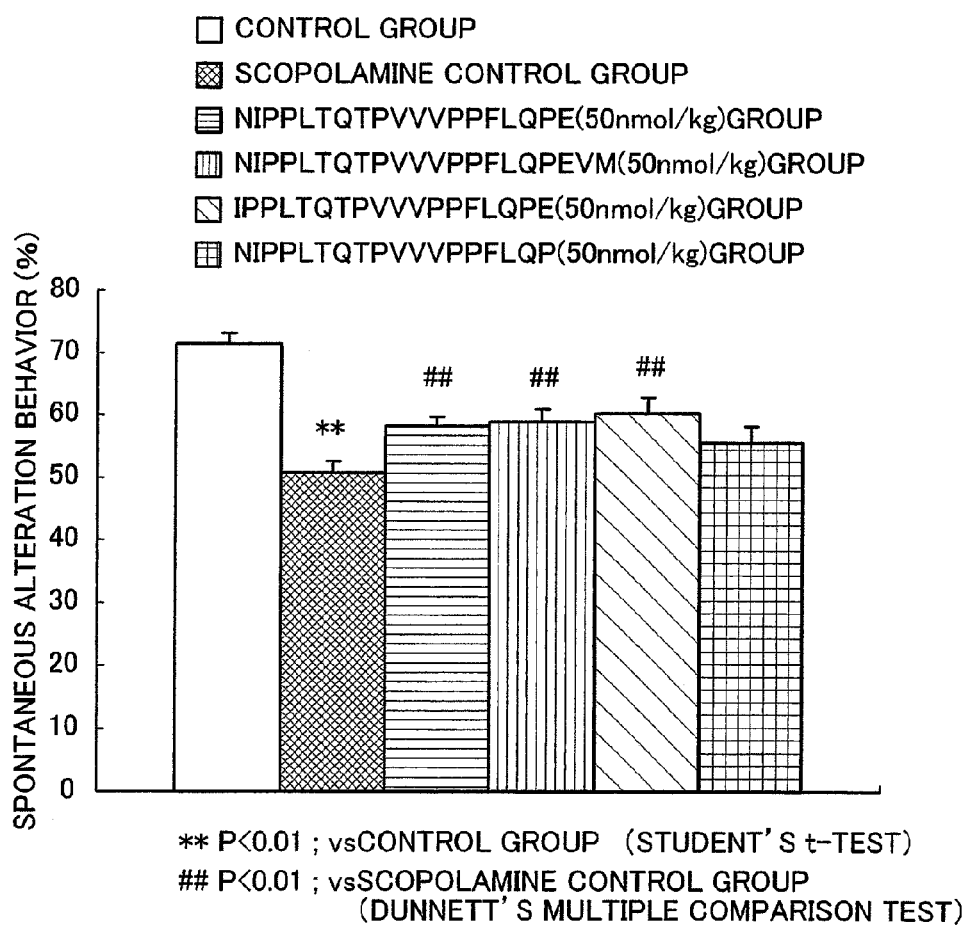
FIG. 2 shows a prophylactic effect of each of peptides Asn-Ile-Pro-Pro-Leu-Thr-Gln-Thr- Pro-Val-Val-Val-Pro-Pro-Phe-Leu-Gln-Pro-Glu (NIPPLTQTPVVVPPFLQPE) (SEQ ID NO: 3), Asn-Ile-Pro-Pro-Leu-Thr-Gln-Thr-Pro-Val-Val-Val-Pro-Pro-Phe-Leu-Gln-Pro-Glu-Val-Met (NIPPLTQTPVVVPPFLQPEVM) (SEQ ID NO:6), Ile-Pro-Pro-Leu-Thr-Gln-Thr-Pro-Val-Val -Val-Pro-Pro-Phe-Leu-Gln-Pro-Glu (IPPLTQTPVVVPPFLQPE) (SEQ ID NO: 2), Asn-Ile-Pro -Pro-Leu-Thr-Gln-Thr-Pro-Val-Val-Pro-Pro-Phe-Leu-Gln-Pro (NIPPLTQTPVVVPPFLQP) (SEQ ID NO: 18) against scopolamine-induced amnesia. Water (control), scopolamine alone, or 50 nmol/kg weight of NIPPLTQTPVVVPPFLQPE (SEQ ID NO: 3), 50 nmol/kg weight of NIPPLTQTPVVVPPFLQPEVM (SEQ ID NO:6), 50 nmol/kg weight of IPPLTQTPVVVPPFLQPE (SEQ ID NO: 2), or 50 nmol/kg weight of NIPPLTQTPVVVPPFLQP (SEQ ID NO: 18) together with scopolamine was administered to mice, and their respective prophylactic effects against amnesia were evaluated in accordance with a method described in Example 2. The vertical axis in FIG. 2 shows the percentage of spontaneous alternation behavior. In order to confirm whether or not amnesia was induced, a significant difference between the water-administered control group and the scopolamine control group to which scopolamine was administered alone was calculated using Student's t-test. ** indicates P<0.01 with respect to the water-administered control group. A significant difference between the peptide-administered groups and the scopolamine control group was calculated using Dunnett's multiple comparison test. ## indicates P<0.01 with respect to the scopolamine control group.

Prophylactic Activity of Asn-Ile-Pro-Pro-Leu-Thr-Gln-Thr-Pro-Val-Val-Val-Pro-Pro-Phe-Leu-Gln-Pro-Glu NIPPLTQTPVVVPPFLQPE)-Related Peptides Against Amnesia Male mice (n=15 to 45) of the ddY strain (approximately 7-week old) were used, and they received food and water ad lib. Test substances used were: 50 nmol/kg weight (100 µg/kg weight) of Asn-Ile-Pro-Pro-Leu-Thr-Gln-Thr-Pro-Val-Val-Val-Pro-Pro-Phe-Leu-Gln-Pro-Glu; 50 nmol/kg weight (120 µg/kg weight) of Asn-Ile-Pro-Pro-Leu-Thr-Gln-Thr-Pro-Val-Val-Val-Pro-Pro-Phe-Leu-Gln-Pro-Glu-Val-Met (NIPPLTQTPVVVPPFLQPEVM); 50 nmol/kg weight (100 µg/kg weight) of Ile-Pro-Pro-Leu-Thr-Gln-Thr-Pro-Val-Val-Val-Pro-Pro-Phe-Leu-Gln-Pro-Glu (IPPLTQTPVVVPPFLQPE); 50 nmol/kg weight (100 µg/kg weight) of Asn-Ile-Pro-Pro-Leu-Thr-Gln-Thr-Pro-Val-Val-Val-Pro-Pro-Phe-Leu-Gln-Pro (NIPPLTQTPVVVPPFLQP) (SEQ ID NO: 18); and 50 nmol/kg weight (50 µg/kg weight) of Thr-Gln-Thr-Pro-Val-Val-Val-Pro-Pro-Phe (TQTPVVVPPF) (SEQ ID NO: 19). The test substances were administered to the mice once orally 60 minutes before the execution of a Y-shaped maze test for evaluation of spontaneous alternation behavior. Further, 30 minutes before the execution of the Y-shaped maze test, 1 mg/kg weight of scopolamine was subcutaneously administered on the backs of the mice in order to induce brain dysfunction (dysmnesia and/or cognitive impairment) in the mice. In the Y-shaped maze test, a Y-shaped maze was used as an experimental device, in which the length of each arm was 40 cm, the height of the wall was 12 cm, the width of the floor was 3 cm, and the width of the upper part was 10 cm, and three arms were connected to each other at an angle of 120 degrees. Each of the mice was placed at the tip of any one of the arms of the Y-shaped maze, and then let go to freely explore in the maze for 8 minutes. The sequence of the arms each of the mice entered was recorded. The number of entries by each of the mice for each of the arms during the measurement time was counted to be the total number of entries. In the sequence, the combination in which three different arms were selected in succession (for example, with the three arms respectively called A, B, and C, if the sequence of the arms entered is ABCBACACB, the count is 4 inclusive of overlapping) was investigated, and the number of the count was used as the number of spontaneous alternation behavior. The percentage of spontaneous alternation behavior was calculated by dividing the number of spontaneous alternation behavior by a number obtained by subtracting 2 from the total number of entries, and multiplying a resultant number by 100. The percentage of spontaneous alternation behavior was used as an indicator. A higher value of the indicator suggested better maintenance of short-term memory. The measured values were expressed in the form of mean±standard error for each group. A significant difference between the control group and the scopolamine control group was calculated using Student's t-test. Further, a significant difference between the scopolamine control group and the peptide-administered groups was calculated using Dunnett's multiple comparison test after one-way analysis of variance. Results are shown in FIG. 2. It was suggested that 50 nmol/kg weight (100 µg/kg weight) of NIPPLTQTPVVVPPFLQPE, 50 nmol/kg weight (120 µg/kg weight) of NIPPLTQTPVVVPPFLQPEVM, and 50 nmol/kg weight (100 µg/kg weight) of IPPLTQTPVVVPPFLQPE had a prophylactic activity against amnesia. As to 50 nmol/kg weight (100 µg/kg weight) of NIPPLTQTPVVVPPFLQP and 50 nmol/kg weight (50 µg/kg weight) of TQTPVVVPPF, no significant difference was observed in comparison with the scopolamine control group, and did not show any prophylactic activity against amnesia.

EXAMPLE 3

Figure 3:
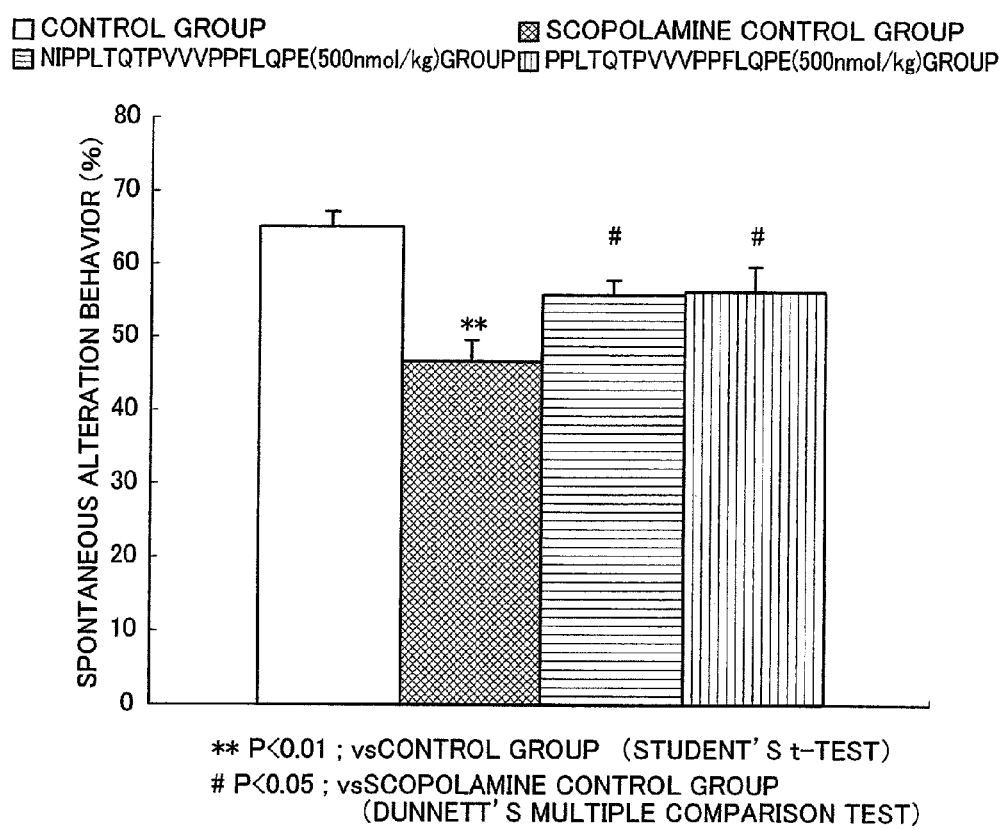
FIG. 3 shows a prophylactic effect of each of peptides Asn-Ile-Pro-Pro-Leu-Thr-Gln-Thr- Pro-Val-Val-Val-Pro-Pro-Phe-Leu-Gln-Pro-Glu (NIPPLTQTPVVVPPFLQPE) (SEQ ID NO: 3) and Pro-Pro-Leu-Thr-Gln-Thr-Pro-Val-Val-Val-Pro-Pro-Phe-Leu-Gln-Pro-Glu-Val-Met (PPLTQTPVVVPPFLQPE) (SEQ ID NO: 1) against scopolamine-induced amnesia. Water (control), scopolamine alone, or 500 nmol/kg weight of NIPPLTQTPVVVPPFLQPE (SEQ ID NO. 3)or 500 nmol/kg of PPLTQTPVVVPPFLQPE together with scopolamine was administered to mice, and their respective prophylactic effects against amnesia were evaluated in accordance with a method described in Example 3. The vertical axis in FIG. 3 shows the percentage of spontaneous alternation behavior. In order to confirm whether or not amnesia was induced, a significant difference between the water-administered control group and the scopolamine control group to which scopolamine was administered alone was calculated using Student's t-test. ** indicates P<0.01 with respect to the water-administered control group. A significant difference between the peptide-administered groups and the scopolamine control group was calculated using Dunnett's multiple comparison test. # indicates P<0.05 with respect to the scopolamine control group.

Prophylactic Activity of Asn-Ile-Pro-Pro-Leu-Thr-Gln-Thr-Pro-Val-Val-Val-Pro-Pro-Phe-Leu-Gln-Pro-Glu (NI PPLTQTPVVVPPFLQPE)—Related Peptides Against Amnesia Male mice (n=14 to 15) of the ddY strain (approximately 7-week old) were used, and they received food and water ad lib. Test substances used were: 500 nmol/kg weight (1000 µg/kg weight) of Asn-Ile-Pro-Pro-Leu-Thr-Gln-Thr-Pro-Val-Val-Val-Pro-Pro-Phe-Leu-Gln-Pro-Glu; and 500 nmol/kg weight (1000 µg/kg weight) of Pro-Pro-Leu-Thr-Gln-Thr-Pro-Val-Val-Val-Pro-Pro-Phe-Leu-Gln-Pro-Glu (PPLTQTPVVVPPFLQPE). The test substances were administered to the mice once orally 60 minutes before the execution of a Y-shaped maze test for evaluation of spontaneous alternation behavior. Further, 30 minutes before the execution of the Y-shaped maze test, 1 mg/kg weight of scopolamine was subcutaneously administered on the backs of the mice in order to induce brain dysfunction (dysmnesia and/or cognitive impairment) in the mice. In the Y-shaped maze test, a Y-shaped maze was used as an experimental device, in which the length of each arm was 40 cm, the height of the wall was 12 cm, the width of the floor was 3 cm, and the width of the upper part was 10 cm, and three arms were connected to each other at an angle of 120 degrees. Each of the mice was placed at the tip of any one of the arms of the Y-shaped maze, and then let go to freely explore in the maze for 8 minutes. The sequence of the arms each of the mice entered was recorded. The number of entries by each of the mice for each of the arms during the measurement time was counted to be the total number of entries. In the sequence, the combination in which three different arms were selected in succession (for example, with the three arms respectively called A, B, and C, if the sequence of the arms entered is ABCBACACB, the count is 4 inclusive of overlapping) was investigated, and the number of the count was used as the number of spontaneous alternation behavior. The percentage of spontaneous alternation behavior was calculated by dividing the number of spontaneous alternation behavior by a number obtained by subtracting 2 from the total number of entries, and multiplying a resultant number by 100. The percentage of spontaneous alternation behavior was used as an indicator. A higher value of the indicator suggested better maintenance of short-term memory. The measured values were expressed in the form of mean±standard error for each group. A significant difference between the control group and the scopolamine control group was calculated using Student's t-test. Further, a significant difference between the scopolamine control group and the peptide-administered groups was calculated using Dunnett's multiple comparison test after one-way analysis of variance. Results are shown in FIG. 3. It was suggested that 500 nmol/kg weight (1000 μg/kg weight) of NIPPLTQTPVVVPPFLQPE and 500 nmol/kg weight (1000 μg/kg weight) of PPLTQTPVVVPPFLQPE had a prophylactic activity against amnesia.

EXAMPLE 4

Memory Strengthening Activity of Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE)

Figure 4:
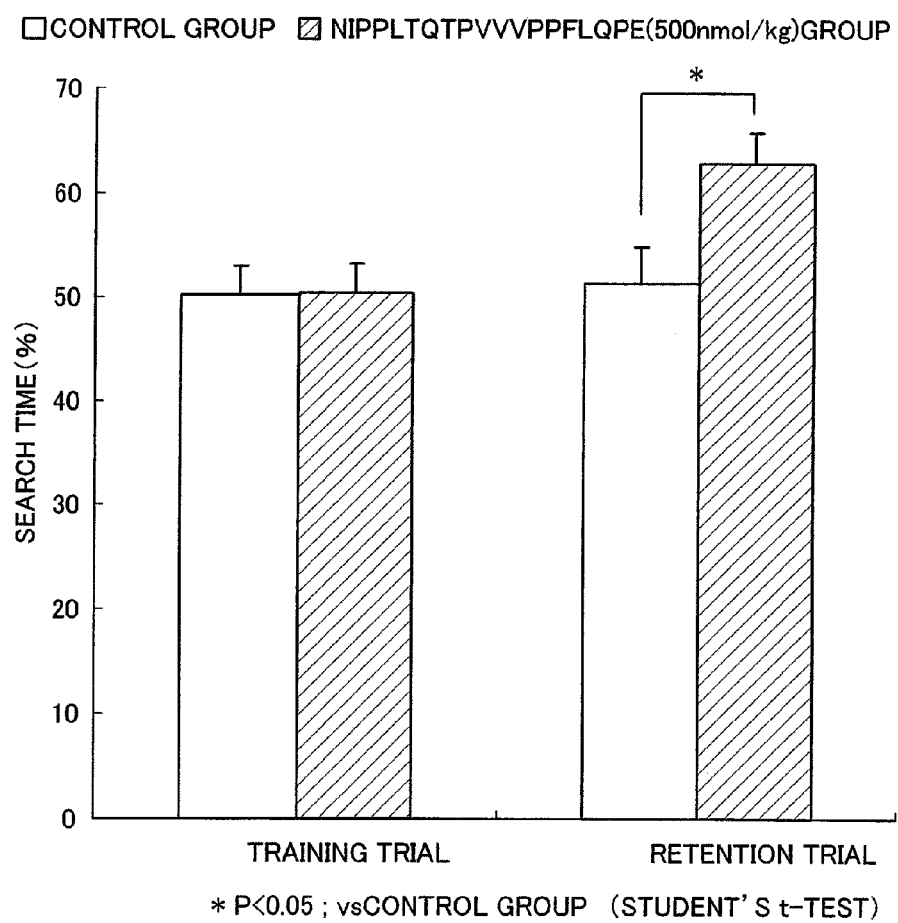
FIG. 4 shows a memory strengthening effect of a peptide Asn-Ile-Pro-Pro-Leu-Thr-Gln- Thr-Pro-Val-Val-Val-Pro-Pro-Phe-Leu-Gln-Pro-Glu (NIPPLTQTPVVVPPFLQPE) (SEQ ID NO: 3). Water (control) or 500 nmol/kg of NIPPLTQTPVVVPPFLQPE (SEQ ID NO: 3)was administered to mice, and their respective memory strengthening effects were evaluated in accordance with a method described in Example 4. The vertical axis in FIG. 4 shows the exploration time ratio. A significant difference between the control group and the peptide group was calculated using Student's t-test, in terms of the exploration time ratio. * indicates P<0.05 with respect to the water-administered control group.

Male mice (n=14 to 15) of the ddY strain (approximately 7-week old) were used, and they received food and water ad lib. A test substance used was 500 nmol/kg weight (1000 μg/kg weight) of Asn-Ile-Pro-Pro-Leu-Thr-Gln-Thr-Pro-Val-Val-Val-Pro-Pro-Phe-Leu-Gln-Pro-Glu. The test substance was administered to the mice once orally 60 minutes before the execution of a novel object recognition test for evaluation of memory maintenance. In the novel object recognition test, a 30 cm x30 cm x30 cm box was used as an experimental device. For acclimation, each of the mice was placed in the experimental device with floor bedding for 5 minutes, and then allo the aminals to go around freely in the device. On the next day of the acclimation treatment, a training trial was performed. In the training trial, two among three kinds of objects were selected and disposed in the experimental device (the objects were arranged along the central line of the floor at positions 8 cm away from the walls on two sides, and the positions were designated as X1 and X2). Note that the objects to be disposed were selected randomly in advance in such a manner as to avoid variations among the animals and between groups. The test substance or water was orally administered to the mice, and 60 minutes later, each of the mice was placed in the experimental device for 5 minutes to measure the time (seconds) each of the mice spent exploring each object by approaching within 1 cm therefrom. A retention trial was performed 48 hours after the training trial. In the retention trial, two objects were disposed in the experimental device as in the training trial, but one of the two objects was replaced with a different object (novel object) from the objects used in the training trial, and the position the novel object was designated as Y (for example, in a case where an object A is disposed at X1 and an object B is disposed at X2 in the training trial, an object C is disposed as a novel object in place of the object A in the retention trial, and the position of object C is designated as Y). In the training trial and the retention trial, the time (seconds) the mice spent exploring each object by approaching within 1 cm therefrom was measured (except the time when the mice were riding on the object). For each of the training trial and the retention trial, an exploration time ratio between the two objects was calculated. The search time ratio (%) between the objects was expressed in the form of mean±standard error for each group. A significant difference between the control group and the peptide group was calculated using Student's t-test, in terms of the exploration time ratio of the novel object (the object disposed at Y) in the retention trial and the exploration time ratio of the object having been disposed at the location where the novel object was disposed (i.e., the object disposed at X1 or X2) in the training trial. Results are shown in FIG. 4. It was suggested that NIPPLTQTPVVVPPFLQPE had a memory strengthening activity at 500 nmol/kg weight (1000 μg/kg weight).

EXAMPLE 5

Figure 5:
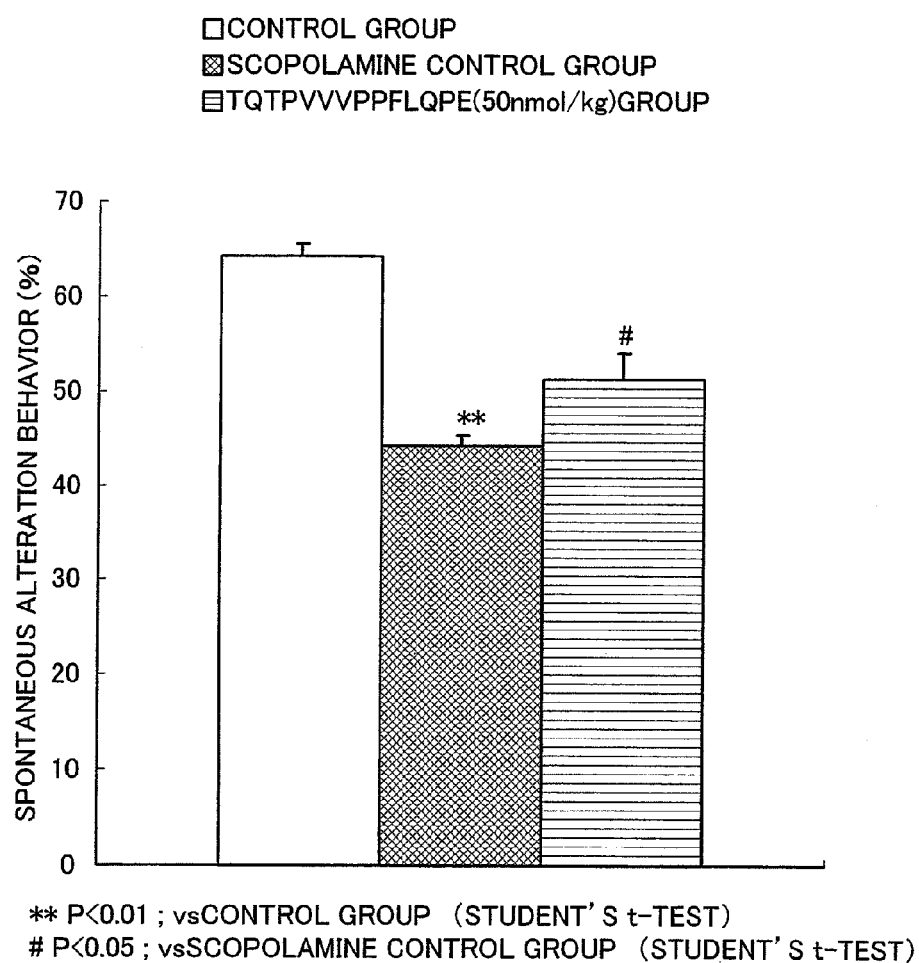
FIG. 5 shows a prophylactic effect of a peptide Thr-Gln-Thr-Pro-Val-Val-Val-Pro-Pro- Phe-Leu-Gln-Pro-Glu (TQTPVVVPPFLQPE) (SEQ ID NO: 7) against scopolamine-induced amnesia. Water (control), scopolamine alone, or 50 nmol/kg weight of TQTPVVVPPFLQPE (SEQ ID NO: 7) together with scopolamine was administered to mice, and their respective prophylactic effects against amnesia were evaluated in accordance with a method described in Example 5. The vertical axis in FIG. 5 shows the percentage of spontaneous alternation behavior. In order to confirm whether or not amnesia was induced, a significant difference between the water-administered control group and the scopolamine control group to which scopolamine was administered alone was calculated using Student's t-test. ** indicates P<0.01 with respect to the water-administered control group. A significant difference between the TQTPVVVPPFLQPE-administered group and the scopolamine control group was calculated using Student's t-test. # indicates P<0.05 with respect to the scopolamine control group.

Prophylactic Activity of Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE)—Related Peptide Against Amnesia Male mice (n=27 to 40) of the ddY strain (approximately 7-week old) were used, and they received food and water ad lib. A test substance used was 50 nmol/kg weight (80 μg/kg weight) of Thr-Gln-Thr-Pro-Val-Val-Val-Pro-Pro-Phe-Leu-Gln-Pro-Glu (TQTPVVVPPFLQPE) (SEQ ID NO: 7). The test substance was administered to the mice once orally 60 minutes before the execution of a Y-shaped maze test for evaluation of spontaneous alternation behavior. Further, 30 minutes before the execution of the Y-shaped maze test, 1 mg/kg weight of scopolamine was subcutaneously administered on the backs of the mice in order to induce brain dysfunction (dysmnesia and/or cognitive impairment) in the mice. In the Y-shaped maze test, a Y-shaped maze was used as an experimental device, in which the length of each arm was 40 cm, the height of the wall was 12 cm, the width of the floor was 3 cm, and the width of the upper part was 10 cm, and three arms were connected to each other at an angle of 120 degrees. Each of the mice was placed at the tip of any one of the arms of the Y-shaped maze, and then let go to freely explore in the maze for 8 minutes. The sequence of the arms each of the mice entered was recorded. The number of entries by each of the mice for each of the arms during the measurement time was counted to be the total number of entries. In the sequence, the combination in which three different arms were selected in succession (for example, with the three arms respectively called A, B, and C, if the sequence of the arms entered is ABCBACACB, the count is 4 inclusive of overlapping) was investigated, and the number of the count was used as the number of spontaneous alternation behavior. The percentage of spontaneous alternation behavior was calculated by dividing the number of spontaneous alternation behavior by a number obtained by subtracting 2 from the total number of entries, and multiplying a resultant number by 100. The percentage of spontaneous alternation behavior was used as an indicator. A higher value of the indicator suggested better maintenance of short-term memory. The measured values were expressed in the form of mean±standard error for each group. A significant difference between the control group and the scopolamine control group was calculated using Student's t-test. Further, a significant difference between the scopolamine control group and the TQTPVVVPPFLQPE (SEQ ID NO: 7)-administered group was calculated using Student's t-test. Results are shown in FIG. 5. It was suggested that TQTPVVVPPFLQPE (SEQ ID NO: 7) had a prophylactic activity against amnesia at 50 nmol/kg weight (80 μg/kg weight).

EXAMPLE 6

Figure 6:
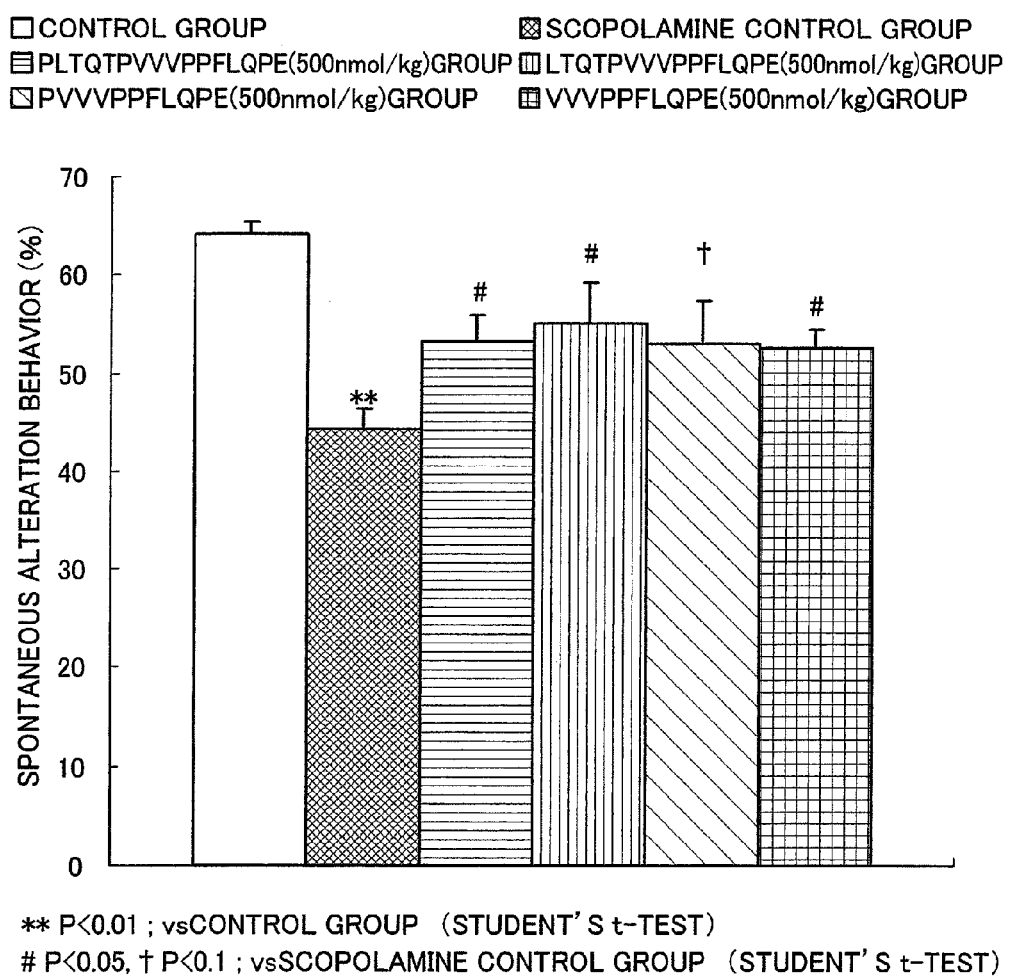
FIG. 6 shows a prophylactic effect of each of peptides Pro-Leu-Thr-Gln-Thr-Pro-Val-Val Val-Pro-Pro-Phe-Leu-Gln-Pro-Glu (PLTQTPVVVPPFLQPE) (SEQ ID NO: 8), Leu-Thr-Gln- Thr-Pro-Val-Val-Val-Pro-Pro-Phe-Leu-Gln-Pro-Glu (LTQTPVVVPPFLQPE) (SEQ ID NO: 9), Pro-Val-Val-Val-Pro-Pro-Phe-Leu-Gln-Pro-Glu(PVVVPPFLQPE) (SEQ ID NO: 10), and Val- Val-Val-Pro-Pro-Phe-Leu-Gln-Pro-Glu (VVVPPFLQPE) (SEQ ID NO: 11)against scopolamine-induced amnesia. Water (control), scopolamine alone, or 500 nmol/kg weight of PLTQTPVVVPPFLQPE (SEQ ID NO: 8), 500 nmol/kg weight of LTQTPVVVPPFLQPE(SEQ ID NO: 9), 500 nmol/kg weight of PVVVPPFLQPE(SEQ ID NO: 10), or 500 nmol/kg weight of VVVPPFLQPE (SEQ ID NO: 11)together with scopolamine was administered to mice, and their respective prophylactic effects against amnesia were evaluated in accordance with a method described in Example 6. The vertical axis in FIG. 6 shows the percentage of spontaneous alternation behavior. In order to confirm whether or not amnesia was induced, a significant difference between the water-administered control group and the scopolamine control group to which scopolamine was administered alone was calculated using Student's t-test. ** indicates P<0.01 with respect to the water-administered control group. A significant difference between each of the peptide-administered groups and the scopolamine control group was calculated using Student's t-test. # indicates P<0.05 with respect to the scopolamine control group, and † indicates P<0.1 with respect to the scopolamine control group.

Prophylactic Activity of Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE)—Related Peptides Against Amnesia Male mice (n=11 to 40) of the ddY strain (approximately 7-week old) were used, and they received food and water ad lib. Test substances used were: 500 nmol/kg weight (900 μg/kg weight) of Pro-Leu-Thr-Gln-Thr-Pro-Val-Val-Val-Pro-Pro-Phe-Leu-Gln-Pro-Glu (PLTQTPVVVPPFLQPE); 500 nmol/kg weight (850 μg/kg weight) of Leu-Thr-Gln-Thr-Pro-Val-Val-Val-Pro-Pro-Phe-Leu-Gln-Pro-Glu (LTQTPVVVPPF LQPE); 500 nmol/kg weight (630 μg/kg weight) of Pro-Val-Val-Val-Pro-Pro-Phe-Leu-Gln-Pro-Glu (PVVVPPFLQPE); and 500 nmol/kg weight (580 μg/kg weight) of Val-Val-Val-Pro-Pro-Phe-Leu-Gln-Pro-Glu (VVVPPFLQPE). The test substances were administered to the mice once orally 60 minutes before the execution of a Y-shaped maze test for evaluation of spontaneous alternation behavior. Further, 30 minutes before the execution of the Y-shaped maze test, 1 mg/kg weight of scopolamine was subcutaneously administered on the backs of the mice in order to induce brain dysfunction (dysmnesia and/or cognitive impairment) in the mice. In the Y-shaped maze test, a Y-shaped maze was used as an experimental device, in which the length of each arm was 40 cm, the height of the wall was 12 cm, the width of the floor was 3 cm, and the width of the upper part was 10 cm, and three arms were connected to each other at an angle of 120 degrees. Each of the mice was placed at the tip of any one of the arms of the Y-shaped maze, and then let go to freely explore in the maze for 8 minutes. The sequence of the arms each of the mice entered was recorded. The number of entries by each of the mice for each of the arms during the measurement time was counted to be the total number of entries. In the sequence, the combination in which three different arms were selected in succession (for example, with the three arms respectively called A, B, and C, if the sequence of the arms entered is ABCBACACB, the count is 4 inclusive of overlapping) was investigated, and the number of the count was used as the number of spontaneous alternation behavior. The percentage of spontaneous alternation behavior was calculated by dividing the number of spontaneous alternation behavior by a number obtained by subtracting 2 from the total number of entries, and multiplying a resultant number by 100. The percentage of spontaneous alternation behavior was used as an indicator. A higher value of the indicator suggested better maintenance of short-term memory. The measured values were expressed in the form of mean±standard error for each group. A significant difference between the control group and the scopolamine control group was calculated using Student's t-test. Further, a significant difference between the scopolamine control group and each of the peptide-administered groups was calculated using Student's t-test. Results are shown in FIG. 6. It was suggested that 500 nmol/kg weight (900 μg/kg weight) of PLTQTPVVVPPFLQPE, 500 nmol/kg weight (850 μg/kg) of LTQTPVVVPPFLQPE, 500 nmol/kg weight (630 μg/kg) of PVVVPPFLQPE, and 500 nmol/kg weight (580 μg/kg) of VVVPPFLQPE had a prophylactic activity against amnesia.

REFERENCES

1. Japanese Patent No. 3898389
2. Science, 217, 408-414 (1982)

The invention claimed is:

1. A composition for improving brain function, comprising, as an active ingredient, a peptide consisting of the amino acid sequence of X-Pro-Pro-Leu-Thr-Gln-Thr-Pro-Val-Val-Val-Pro-Pro-Phe-Leu-Gln-Pro-Glu-Y (SEQ ID NO: 20) or a salt thereof, wherein
   i. X is Asn-Ile, Y is absent or represents Val-Met, or
   ii. X is absent or represents Ile, and Y is absent.

2. The composition for improving brain function according to claim 1, wherein said active ingredient is a peptide consisting of the amino acid sequence of Pro-Pro-Leu-Thr-Gln-Thr-Pro-Val-Val-Val-Pro-Pro-Phe-Leu-Gln-Pro-Glu (SEQ ID NO:1) or a salt thereof.

3. The composition for improving brain function according to claim 1, wherein said active ingredient is a peptide consisting of the amino acid sequence of Ile-Pro-Pro-Leu-Thr-Gln-Thr-Pro-Val-Val-Val-Pro-Pro-Phe-Leu-Gln-Pro-Glu (SEQ ID NO:2) or a salt thereof.

4. The composition for improving brain function according to claim 1, wherein said active ingredient is a peptide consisting of the amino acid sequence of Asn-Ile-Pro-Pro-Leu-Thr-Gln-Thr-Pro-Val-Val-Val-Pro-Pro-Phe-Leu-Gln-Pro-Glu (SEQ ID NO:3) or a salt thereof.

5. The composition for improving brain function according to claim 1, wherein said active ingredient is a peptide consisting of the amino acid sequence of Asn-Ile-Pro-Pro-Leu-Thr-Gln-Thr-Pro-Val-Val-Val-Pro-Pro-Phe-Leu-Gln-Pro-Glu-Val-Met (SEQ ID NO:6) or a salt thereof.

6. A composition for improving brain function, comprising, as an active ingredient, a peptide consisting of the amino acid sequence of X-Val-Val-Val-Pro-Pro-Phe-Leu-Gln-Pro-Glu-Y (SEQ ID NO: 21) or a salt thereof, wherein
   X is absent or represents Leu-Thr-Gln-Thr-Pro (SEQ ID NO: 24) or Pro
   Y is absent.

7. The composition for improving brain function according to claim 6, wherein said active ingredient is a peptide consisting of the amino acid sequence of Leu-Thr-Gln-Thr-Pro-Val-Val-Val-Pro-Pro-Phe-Leu-Gln-Pro-Glu (SEQ ID NO:9) or a salt thereof.

8. The composition for improving brain function according to claim 6, wherein said active ingredient is a peptide consisting of the amino acid sequence of Pro-Val-Val-Val-Pro-Pro-Phe-Leu-Gln-Pro-Glu (SEQ ID NO:10) or a salt thereof.

9. The composition for improving brain function according to claim 6, wherein said active ingredient is a peptide consisting of the amino acid sequence of Val-Val-Val-Pro-Pro-Phe-Leu-Gln-Pro-Glu (SEQ ID NO:11) or a salt thereof.

10. An isolated polypeptide consisting of the amino acid sequence of X-Pro-Pro-Leu-Thr-Gln-Thr-Pro-Val-Val-Val-Pro-Pro-Phe-Leu-Gln-Pro-Glu-Y (SEQ ID NO: 20) or a salt thereof, wherein i) X is Asn-Ile and Y is absent or represents Val-Met or ii) X is absent or represents Ile and Y is absent.

11. The isolated polypeptide according to claim 10, wherein said polypeptide consists of the amino acid sequence of Asn-Ile-Pro-Pro-Leu-Thr-Gln-Thr-Pro-Val-Val-Val-Pro-Pro-Phe-Leu-Gln-Pro-Glu (SEQ ID NO:3) or a salt thereof.

12. The isolated polypeptide according to claim 10, wherein said polypeptide consists of the amino acid sequence of Asn-Ile-Pro-Pro-Leu-Thr-Gln-Thr-Pro-Val-Val-Val-Pro-Pro-Phe-Leu-Gln-Pro-Glu-Val-Met (SEQ ID NO:6) or a salt thereof.

13. The isolated polypeptide according to claim 10, wherein said polypeptide consists of the amino acid sequence of Pro-Pro-Leu-Thr-Gln-Thr-Pro-Val-Val-Val-Pro-Pro-Phe-Leu-Gln-Pro-Glu (SEQ ID NO:1) or a salt thereof.

14. The isolated polypeptide according to claim 10, wherein said polypeptide consists of the amino acid sequence of Ile-Pro-Pro-Leu-Thr-Gln-Thr-Pro-Val-Val-Val-Pro-Pro-Phe-Leu-Gln-Pro-Glu (SEQ ID NO:2) or a salt thereof.

15. An isolated polypeptide consisting of the amino acid sequence of X-Val-Val-Val-Pro-Pro-Phe-Leu-Gln-Pro-Glu (SEQ ID NO: 25) or a salt thereof, wherein X is absent or represents Leu-Thr-Gln-Thr-Pro (SEQ ID NO: 24) or Pro.

16. The isolated polypeptide according to claim 15, wherein said polypeptide consists of the amino acid sequence of Leu-Thr-Gln-Thr-Pro-Val-Val-Val-Pro-Pro-Phe-Leu-Gln-Pro-Glu (SEQ ID NO:9) or a salt thereof.

17. The isolated polypeptide according to claim 15, wherein said polypeptide consists of the amino acid sequence of Pro-Val-Val-Val-Pro-Pro-Phe-Leu-Gln-Pro-Glu (SEQ ID NO:10) or a salt thereof.

18. The isolated polypeptide according to claim 15, wherein said polypeptide consists of the amino acid sequence of Val-Val-Val-Pro-Pro-Phe-Leu-Gln-Pro-Glu (SEQ ID NO:11) or a salt thereof.

* * * * *

SEQUENCE LISTING

<160> NUMBER OF SEQ ID NOS: 25

<210> SEQ ID NO 1
<211> LENGTH: 17
<212> TYPE: PRT
<213> ORGANISM: Artificial Sequence
<220> FEATURE:
<223> OTHER INFORMATION: Synthetic functional peptide

<400> SEQUENCE: 1

Pro Pro Leu Thr Gln Thr Pro Val Val Val Pro Pro Phe Leu Gln Pro
1               5                   10                  15

Glu

<210> SEQ ID NO 2
<211> LENGTH: 18
<212> TYPE: PRT
<213> ORGANISM: Artificial Sequence
<220> FEATURE:
<223> OTHER INFORMATION: Synthetic functional peptide

<400> SEQUENCE: 2

Ile Pro Pro Leu Thr Gln Thr Pro Val Val Val Pro Pro Phe Leu Gln
1               5                   10                  15

Pro Glu

<210> SEQ ID NO 3
<211> LENGTH: 19

```
<212> TYPE: PRT
<213> ORGANISM: Artificial Sequence
<220> FEATURE:
<223> OTHER INFORMATION: Synthetic functional peptide

<400> SEQUENCE: 3

Asn Ile Pro Pro Leu Thr Gln Thr Pro Val Val Val Pro Pro Phe Leu
1               5                   10                  15

Gln Pro Glu

<210> SEQ ID NO 4
<211> LENGTH: 19
<212> TYPE: PRT
<213> ORGANISM: Artificial Sequence
<220> FEATURE:
<223> OTHER INFORMATION: Synthetic functional peptide

<400> SEQUENCE: 4

Pro Pro Leu Thr Gln Thr Pro Val Val Val Pro Pro Phe Leu Gln Pro
1               5                   10                  15

Glu Val Met

<210> SEQ ID NO 5
<211> LENGTH: 20
<212> TYPE: PRT
<213> ORGANISM: Artificial Sequence
<220> FEATURE:
<223> OTHER INFORMATION: Synthetic functional peptide

<400> SEQUENCE: 5

Ile Pro Pro Leu Thr Gln Thr Pro Val Val Val Pro Pro Phe Leu Gln
1               5                   10                  15

Pro Glu Val Met
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic functional peptide

<400> SEQUENCE: 6

Asn Ile Pro Pro Leu Thr Gln Thr Pro Val Val Val Pro Pro Phe Leu
1               5                   10                  15

Gln Pro Glu Val Met
            20

<210> SEQ ID NO 7
<211> LENGTH: 14
<212> TYPE: PRT
<213> ORGANISM: Artificial Sequence
<220> FEATURE:
<223> OTHER INFORMATION: Synthetic functional peptide

<400> SEQUENCE: 7

Thr Gln Thr Pro Val Val Val Pro Pro Phe Leu Gln Pro Glu
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Synthetic functional peptide
```

```
<400> SEQUENCE: 8

Pro Leu Thr Gln Thr Pro Val Val Val Pro Pro Phe Leu Gln Pro Glu
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic functional peptide

<400> SEQUENCE: 9

Leu Thr Gln Thr Pro Val Val Val Pro Pro Phe Leu Gln Pro Glu
1               5                   10                  15

<210> SEQ ID NO 10
<211> LENGTH: 11
<212> TYPE: PRT
<213> ORGANISM: Artificial Sequence
<220> FEATURE:
<223> OTHER INFORMATION: Synthetic functional peptide

<400> SEQUENCE: 10

Pro Val Val Val Pro Pro Phe Leu Gln Pro Glu
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic functional peptide

<400> SEQUENCE: 11

Val Val Val Pro Pro Phe Leu Gln Pro Glu
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Synthetic functional peptide

<400> SEQUENCE: 12

Thr Gln Thr Pro Val Val Val Pro Pro Phe Leu Gln Pro Glu Val Met
1               5                   10                  15

<210> SEQ ID NO 13
<211> LENGTH: 18
<212> TYPE: PRT
<213> ORGANISM: Artificial Sequence
<220> FEATURE:
<223> OTHER INFORMATION: Synthetic functional peptide

<400> SEQUENCE: 13

Pro Leu Thr Gln Thr Pro Val Val Val Pro Pro Phe Leu Gln Pro Glu
1               5                   10                  15

Val Met

<210> SEQ ID NO 14
<211> LENGTH: 17
<212> TYPE: PRT
<213> ORGANISM: Artificial Sequence
<220> FEATURE:
<223> OTHER INFORMATION: Synthetic functional peptide
```

-continued

```
<400> SEQUENCE: 14

Leu Thr Gln Thr Pro Val Val Val Pro Pro Phe Leu Gln Pro Glu Val
1               5                   10                  15

Met

<210> SEQ ID NO 15
<211> LENGTH: 13
<212> TYPE: PRT
<213> ORGANISM: Artificial Sequence
<220> FEATURE:
<223> OTHER INFORMATION: Synthetic functional peptide

<400> SEQUENCE: 15

Pro Val Val Val Pro Pro Phe Leu Gln Pro Glu Val Met
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic functional peptide

<400> SEQUENCE: 16

Val Val Val Pro Pro Phe Leu Gln Pro Glu Val Met
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Synthetic functional peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 17

Xaa Pro Leu Pro Arg
1               5

<210> SEQ ID NO 18
<211> LENGTH: 18
<212> TYPE: PRT
<213> ORGANISM: Artificial Sequence
<220> FEATURE:
<223> OTHER INFORMATION: Synthetic comparative example

<400> SEQUENCE: 18

Asn Ile Pro Pro Leu Thr Gln Thr Pro Val Val Val Pro Pro Phe Leu
1               5                   10                  15

Gln Pro

<210> SEQ ID NO 19
<211> LENGTH: 10
<212> TYPE: PRT
<213> ORGANISM: Artificial Sequence
<220> FEATURE:
<223> OTHER INFORMATION: Synthetic comparative example

<400> SEQUENCE: 19

Thr Gln Thr Pro Val Val Val Pro Pro Phe
1               5                   10

<210> SEQ ID NO 20
```

```
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa, if present, is Ile or Asn-Ile
<220> FEATURE:
<221> NAME/KEY: misc_feature
<222> LOCATION: (20)..(21)
<223> OTHER INFORMATION: Xaa, if present, is Val-Met

<400> SEQUENCE: 20

Xaa Xaa Pro Pro Leu Thr Gln Thr Pro Val Val Val Pro Pro Phe Leu
1               5                   10                  15

Gln Pro Glu Xaa Xaa
            20

<210> SEQ ID NO 21
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(6)
<223> OTHER INFORMATION: Xaa, if present, can be Thr-Gln-Thr-Pro,
      Pro-Leu-Thr-Gln-Thr-Pro, Leu-Thr-Gln-Thr-Pro, or Pro
<220> FEATURE:
<221> NAME/KEY: misc_feature
<222> LOCATION: (17)..(18)
<223> OTHER INFORMATION: Xaa, if present, is Val-Met

<400> SEQUENCE: 21

Xaa Xaa Xaa Xaa Xaa Xaa Val Val Val Pro Pro Phe Leu Gln Pro Glu
1               5                   10                  15

Xaa Xaa

<210> SEQ ID NO 22
<211> LENGTH: 4
<212> TYPE: PRT
<213> ORGANISM: Artificial Sequence
<220> FEATURE:
<223> OTHER INFORMATION: Synthetic peptide

<400> SEQUENCE: 22

Thr Gln Thr Pro
1

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide

<400> SEQUENCE: 23

Pro Leu Thr Gln Thr Pro
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide
```

```
<400> SEQUENCE: 24

Leu Thr Gln Thr Pro
1               5

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: Xaa, if present, can be Leu-Thr-Gln-Thr-Pro or
      Pro

<400> SEQUENCE: 25

Xaa Xaa Xaa Xaa Xaa Val Val Val Pro Pro Phe Leu Gln Pro Glu
1               5                   10                  15
```